United States Patent [19]

Place et al.

[11] Patent Number: 4,677,128
[45] Date of Patent: Jun. 30, 1987

[54] (ARYLTHIO)-PYRIDYLALKANOLS AND THEIR USE AS FUNGICIDES

[75] Inventors: Pierre Place, Charly Vernaison; Claude Anding, Chaponost; Jean-Claude Debourge, Champagne Au Mont D'Or, all of France

[73] Assignee: Rhone-Poulenc Agrochimie, Lyons, France

[21] Appl. No.: 705,558

[22] Filed: Feb. 26, 1985

[30] Foreign Application Priority Data

Mar. 15, 1984 [FR] France ................................. 84 04235

[51] Int. Cl.⁴ .................. C07D 211/70; C07D 211/82; C07D 213/26; C07D 213/28
[52] U.S. Cl. ........................ 514/277; 546/344; 546/330; 546/329; 546/343
[58] Field of Search ............... 546/344, 330, 329, 343; 514/277

[56] References Cited

U.S. PATENT DOCUMENTS 3,849,423 11/1974 Krumkains et al. ................. 546/344
3,869,456 3/1975 Taylor et al. ........................ 546/344
4,438,122 3/1984 Holmwood et al. ................. 546/344

FOREIGN PATENT DOCUMENTS 0001399 9/1978 European Pat. Off. ............ 546/344
0074018 8/1982 European Pat. Off. ............ 546/344
2130555 3/1972 France ............................... 546/344

OTHER PUBLICATIONS

Malinovski, Epoxides and Their Derivatives, Davey & Co., Inc., New York, N.Y., 1965, p. 193.

Primary Examiner—Henry R. Jiles
Assistant Examiner—Robert C. Whittenbaugh
Attorney, Agent, or Firm—Scully, Scott, Murphy & Presser

[57] ABSTRACT (Arylthio)pyridylalkanol derivatives of the formula:

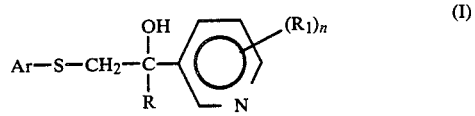

in which:
Ar denotes an optionally substituted aryl radical,
R denotes a hydrogen atom or an optionally substituted alkyl radical, an optionally substituted aryl radical or an optionally substituted aralkyl radical,
$R_1$ denotes an alkyl radical, and n equals 0, 1, 2, 3 or 4.

6 Claims, No Drawings

(ARYLTHIO)-PYRIDYLALKANOLS AND THEIR USE AS FUNGICIDES

The present invention relates to new (arylthio)-pyridylalkanols, the preparation of these products and also their application for the protection of plants, especially in the field of controlling parasitic fungi.

An object of the invention is the production of products for use in plant protection, in particular as fungicides, provided with 3-pyridine groups and substituted sulphur, which are active against fungi of the Botrytis type. Another object of the invention is to provide fungicides which have a broad spectrum of activity. It has now been found that these objects could be attained by means of the products of the invention. These products are of the formula (I):

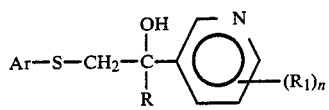  (I)

in which:
Ar denotes an optionally substituted aryl radical,
R denotes a hydrogen atom or an optionally substituted alkyl radical, preferably branched, an optionally substituted aryl radical or an optionally substituted aralkyl radical,
$R_1$ denotes a linear or branched alkyl radical,
n is an integer equal to 0, 1, 2, 3 or 4, on the understanding that when n is greater than 1, the substituents $R_1$ can be identical or different.

Advantageously, Ar denotes an aryl radical containing 6 to 10 carbon atoms (for example a phenyl radical or naphthyl radical), optionally substituted with one or more identical or different substituents.

Substituents on this aryl radical can be chosen from: halogen atoms (preferably chlorine, fluorine or bromine), alkyl radicals containing 1 to 12 carbon atoms (for example methyl, ethyl, isobutyl, and the like), optionally mono- or polyhalogenated (for example trifluoromethyl), alkenyl and alkynyl radicals containing 3 to 12 carbon atoms (for example allyl, propargyl), alkoxy and alkylthio radicals containing 1 to 6 carbon atoms (for example methoxy, methylthio, ethoxy, isopropoxy, and the like), optionally mono- or polyhalogenated (for example trifluoromethoxy, trifluoromethylthio); cyano radicals; nitro radicals; optionally substituted phenyl radicals (for example mono- or polyhalogenated phenyl radicals); optionally substituted benzyl radicals; optionally substituted phenoxy radicals; and optionally substituted amino radicals (for example amino radicals substituted with 1 to 2 radicals chosen from alkyl radicals containing 1 to 6 carbon atoms and alkanoyl radicals containing 2 to 6 carbon atoms).

Advantageously, R denotes a hydrogen atom or an alkyl radical containing 1 to 10 carbon atoms (preferably a branched alkyl radical containing 3 to 5 carbon atoms, such as isopropyl, secondary butyl, tert-butyl) or a phenyl or benzyl radical, these phenyl and benzyl radicals being optionally substituted (for example with one or more halogen atoms or with one or more alkyl radicals each containing 1 to 6 carbon atoms and themselves optionally substituted).

Advantageously, $R_1$ denotes an alkyl radical containing 1 to 6 carbon atoms (for example methyl, ethyl, isopropyl, t-butyl, and the like) and n equals 0, 1 or 2.

The compounds according to the invention can exist in one or more optical isomeric forms. The invention hence relates both to these optical isomers and to racemic mixtures thereof.

In the case where there are two asymmetric carbon atoms, the compounds according to the invention can exist in the form of diastereoisomers, which are also included within the scope of the present invention.

The invention also relates to the salified forms of the compounds according to the invention, and more especially the hydrochlorides, sulphates and oxalates.

The present invention also relates to a process for preparing the compounds according to the invention.

According to this process, the compounds of formula (I) can be prepared by reacting a thiolate of formula (II):

  (II)

in which Ar has the same significance as in formula (I) and alk is an alkali metal atom, preferably sodium or potassium, with a pyridine containing an epoxy group of formula (III):

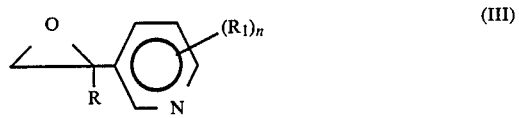  (III)

in which R, $R_1$ and n have the same significance as in the formula (I).

The compound of formula (II) can be prepared in situ or otherwise from an aromatic thiol of formula (IV):

  (IV)

in which Ar has the same significance as in the formula (II), by the action of alkali metal agents, for example alkali metal hydroxides, carbonates or hydrides.

The compounds of formula (III) can be prepared according to the process desribed in J. Chem. Soc. Perkin Trans. J. 1982 (2), 587 to 590, by reacting a (dimethyl)oxosulphonium or dimethylsulphonium salt in the presence of a base with a ketone of formula (V):

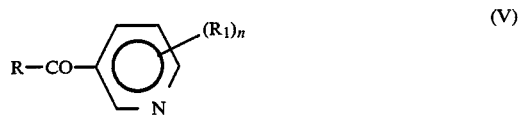  (V)

in which R, $R_1$ and n have the same significance as in the formula (III).

The reaction between the compounds of formula (II) and (III) is generally performed at between $-20°$ and $+120°$ C., preferably between 20° and 80° C. The reaction time can vary within broad limits, e.g. 1 to 50 h, or more frequently between 1 and 5 h.

The compounds of formula (II) and (III) are advantageously used in stoichiometric proportions, but they can also be used in amounts which depart from the stoichiometry, e.g. up to 100% molar excess of thiolate of formula (II).

It is advantageous to work in a polar solvent.

As solvents which are capable of being used, there may be mentioned aprotic polar solvents such as dimethylformamide (DMF), dimethyl sulphoxide (DMSO); nitriles such as acetonitrile; and hydroxylated solvents such as alcohols which are liquid at room temperature, in particular ethanol.

At the end of the reaction, the compound of formula (I) can be isolated by any means known per se, e.g. by evaporation of the reaction medium followed by extraction with a solvent immiscible with water, such as for example esters (ethyl acetate or the like) or halogenated hydrocarbons (chloroform, dichloromethane).

The ketones of formula (V) can be prepared according to one or other of the known processes described in J. Am. Chem. Soc. 1951, 73, 469, Synthesis 1980, p. 1009, Org. Synth. Coll. Vol. IV 1963 p. 88, and more especially by hydrolysis of alpha-pyridyl-alpha-morpholinoacetonitriles of formula (VI):

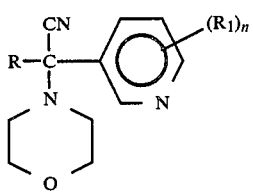  (VI)

in which R, $R_1$ and n have the same significance as in the formula (V), working according to the process described in J. Org. Chem. 1979, 44 (25), p. 4596.

The compounds of formula (VI) can be obtained by the action of the halide of formula (VII):

 R—hal    (VII)

in which R has the same significance as in the formula (VI) and hal denotes a halogen atom, on the compound of formula (VIII):

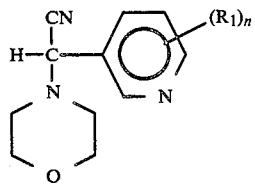  (VIII)

in which $R_1$ and n have the same significance as above, working according to the process described in J. Org. Chem. 1979, 44 (25), p. 4597.

The compound of the formula (V), for which R denotes a tert-butyl radical and n equals zero, can be advantageously prepared by methylating the compound of formula (V) for which R denotes an isopropyl radical (e.g., by the action of $ICH_3$ in DMF in the presence of NaH). This compound can also be prepared by oxidation of the alcohol of formula (IX):

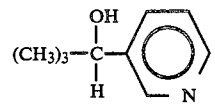  (IX)

working according to the method described in U.S. Pat. No. 4,098,908.

The alcohol of formula (IX) is advantageously prepared by reacting the magnesium derivative of tert-butylchloride in an ether solvent, e.g. ethyl ether or THF, with 3-pyridinecarboxaldehyde.

The examples which follow, which are given without implied limitation, illustrate the invention and show how it can be used.

Examples 1 to 63 and Table I illustrate the preparation of the compounds according to the invention.

Examples 64 to 67 and Table II illustrate the fungicidal properties of the compounds according to the invention.

In Examples 64 to 66, the spraying of solutions or suspensions of active substances is performed under conditions such that the spraying of a solution or suspension of concentration equal to 1 g/l corresponds on average to the application of approximately 2 micrograms of active substance per $cm^2$ of plant leaf.

In these examples, a product is regarded as providing complete protection against a fungal disease when the protection is at least 95%; the protection is regarded as good when it is at least 80% (but less than 95%), as fairly good when it is at least 70% (but less than 80%) and as average when it is at least 50% (but less than 70%).

In the present account, the percentages are, except where otherwise stated and except in regard to yields, percentages by weight. In the case of percentages expressed relative to the stoichiometry, these are molar percentages. As regards concentrations, some of these are expressed in ppm (parts per million) which corresponds to mg/l.

EXAMPLE 1

Preparation of 3,3-dimethyl-1-(4-methylphenylthio)-2-(3-pyridyl)-2-butanol

To a solution of sodium 4-methylthiophenate (4.38 g; 0.03 mol) in DMF (40 ml) a solution of 3,3-dimethyl-1,2-epoxy-2-(3-pyridyl)butane (2.75 g; 0.016 mol), of formula:

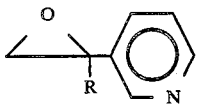

in DMF (40 ml) is added in the course of 2 min at 20° C.

The mixture is heated to 40° C. for one hour. The reaction mixture is then poured into cold water (200 ml) and this mixture is then extracted with ethyl acetate (3×50 ml). The organic phase is washed twice with water and the solvent then concentrated under vacuum.

After recrystallisation of the solid obtained in hexane, the compound sought (2.6 g), of formula:

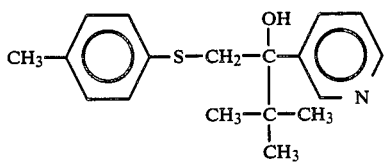

is obtained in the form of a white solid, m.p. 67° C. (57% yield).

The structure of this compound was confirmed by nuclear magnetic resonance (NMR). The spectrum obtained in deuterated chloroform, with tetramethylsilane as internal reference, is as follows:

a singlet at 0.95 ppm (9H), a singlet at 2.29 ppm (3H), a doublet at 3.33 ppm (1H), a doublet at 4.44 ppm (1H), a complex at 7.10 ppm (5H), a complex at 7.70 ppm (1H), a complex at 8.46 ppm (1H), a doublet at 8.64 ppm (1H).

EXAMPLES 2 to 63

By working according to the method of Example no. 1, starting from suitable starting materials, the compounds nos. 2 to 63 below were prepared:

No. 2: 2-(4-bromophenylthio)-1-(3-pyridyl)ethanol,
No. 3: 1-(3-pyridyl)-2-[4-(trifluoromethyl)phenylthio]ethanol,
No. 4: 1-(4-chlorophenylthio)-2-(3-pyridyl)-2-propanol,
No. 5: 2-(3-pyridyl)-1-[4-(trifluoromethyl)phenylthio]-2-propanol,
No. 6: 1-(4-bromophenylthio)-2-(3-pyridyl)-2-propanol,
No. 7: 1-(4-methylphenylthio)-2-(3-pyridyl)-2-propanol,
No. 8: 1-(2,4-dichlorophenylthio)-2-(3-pyridyl)-2-propanol,
No. 9: 1-(beta-naphthylthio)-2-(3-pyridyl)-2-propanol,
No. 10: 2-(beta-naphthylthio)-1-phenyl-1-(3-pyridyl)ethanol,
No. 11: 2-(4-chlorophenylthio)-1-phenyl-1-(3-pyridyl)ethanol,
No. 12: 1-phenyl-1-(3-pyridyl)-2-[4-(trifluoromethyl)phenylthio]ethanol,
No. 13: 2-(4-bromophenylthio)-1-phenyl-1-(3-pyridyl)ethanol,
No. 14: 1-(4-chlorophenyl)-2-(beta-naphthylthio)-1-(3-pyridyl)ethanol,
No. 15: 2-(4-chlorophenylthio)-1-(4-chlorophenyl)-1-(3-pyridyl)ethanol,
No. 16: 2-(4-bromophenylthio)-1-(4-chlorophenyl)-1-(3-pyridyl)ethanol,
No. 17: 1-(4-chlorophenyl)-2-(4-methylphenylthio)-1-(3-pyridyl)ethanol,
No. 18: 1-(4-bromophenyl)-2-(4-chlorophenylthio)-1-(3-pyridyl)ethanol,
No. 19: 1-(4-bromophenyl)-2-(4-methylphenylthio)-1-(3-pyridyl)ethanol,
No. 20: 1-(4-bromophenyl)-2-(4-bromophenylthio)-1-(3-pyridyl)ethanol,
No. 21: 1-(4-bromophenyl)-2-phenylthio-1-(3-pyridyl)ethanol, No. 22: 1-(4-bromophenyl)-2-(3-chloro-4-methylphenylthio)-1-(3-pyridyl)ethanol
No. 23: 1-(4-bromophenylthio)-3-methyl-2-(3-pyridyl)-2-butanol,
No. 24: 3-methyl-2-(3-pyridyl)-1-[4-(trifluoromethyl)phenylthio]2-butanol,
No. 25: 1-(4-chlorophenylthio)-3-methyl-2-(3-pyridyl)-2-butanol,
No. 26: 1-(4-bromophenylthio)-4-methyl-2-(3-pyridyl)-2-pentanol,
No. 27: 1-(4-chlorophenylthio)-4-methyl-2-(3-pyridyl)-2-pentanol,
No. 28: 4-methyl-2-(3pyridyl)-1-[4-trifluoromethyl)-phenylthio]-2-pentanol,
No. 29: 2-(4-chlorophenylthio)-1-(3-pyridyl)ethanol,
No. 30: 1-(4-chlorophenylthio)-3,3-dimethyl-2-(3-pyridyl)-2-butanol,
No. 31: 1-(4-bromophenylthio)-3,3-dimethyl-2-(3-pyridyl)-2-butanol,
No. 32: 1-(3,5-dichlorophenylthio)-3,3-dimethyl-2-(3-pyridyl)-2-butanol,
No. 33: 3,3-dimethyl-1-(4-fluorophenylthio)-2-(3-pyridyl)-2-butanol,
No. 34: 1-(4-chloro-2-methylphenylthio)-3,3-dimethyl-2-(3-pyridyl)-2-butanol,
No. 35: 3,3-dimethyl-1-(beta-naphthylthio)-2-(3-pyridyl)-2-butanol,
No. 36: 1-(4-chlorophenylthio)-3-methyl-2-(3-pyridyl)-2-pentanol,
No. 37: 1-(4-bromophenylthio)-3-methyl-2-(3-pyridyl)-2-pentanol,
No. 38: 1-(4-methylphenylthio)-3-methyl-2-(3-pyridyl)-2-pentanol,
No. 39: 1-(4-chloro-2-methylphenylthio)-3-methyl-2-(3-pyridyl)-2-pentanol,
No. 40: 1-(4-methoxyphenylthio)-3-methyl-2-(3-pyridyl)-2-pentanol,
No. 41: 1-(4-fluorophenylthio)-3-methyl-2-(3-pyridyl)-2-pentanol,
No. 42: 1-(4-n-dodecylphenylthio)-3-methyl-2-(3-pyridyl)-2-pentanol,
No. 43: 3-methyl-1-(4-n-nonylphenylthio)-2-(3-pyridyl)-2-pentanol,
No. 44: 3-methyl-2-(3-pyridyl)-1-[4-(trifluoromethyl)phenylthio]-2-pentanol,
No. 45: 3-methyl-2-(3-pyridyl)-1-(2,4,5-trichlorophenylthio)-2-pentanol,
No. 46: 3-methyl-1-(beta-naphthylthio)-2-(3-pyridyl)-2-pentanol,
No. 47: 3,3-dimethyl-1-(4-n-dodecylphenylthio)-2-(3-pyridyl)-2-butanol,
No. 48: 3,3-dimethyl-1-(4-n-nonylphenylthio)-2-(3-pyridyl)-2-butanol,
No. 49: 1-(2,4-dichlorophenylthio)-3,3-dimethyl-2-(3-pyridyl)-2-butanol,
No. 50: 3,3-dimethyl-1-(beta-naphthylthio)-2-(pyridyl)-2-pentanol,
51: 3,3-dimethyl-1-(4-fluorophenylthio)-2-(3-pyridyl)-2-pentanol,
No. 52: 3,3-dimethyl-1-(4-n-dodecylphenylthio)-2-(3-pyridyl)-2-pentanol,
No. 53: 3,3-dimethyl-1-(4-n-nonylphenylthio)-2-(3-pyridyl)-2-pentanol,
No. 54: 1-(4-bromophenylthio)-3,3-dimethyl-2-(3-pyridyl)-2-pentanol,
No. 55: 1-(4-chlorophenylthio)-3,3-dimethyl-2-(3-pyridyl)-2-pentanol,
No. 56: 3,3-dimethyl-1-(4-methylphenylthio)-2-(3-pyridyl)-2-pentanol,
No. 57: 3,3-dimethyl-1-(4-methoxyphenylthio)-2-(3-pyridyl)-2-pentanol,
No. 58: 1-(4-chlorophenylthio)-3-methyl-2-(3-pyridyl)-2-hexanol,
No. 59: 1-(4-bromophenylthio)-3-methyl-2-(3-pyridyl)-2-hexanol,
No. 60: 3-methyl-2-(3-pyridyl)-1-[4-(trifluoromethyl)phenylthio]-2-hexanol,
No. 61: 1-(4-bromophenylthio)-3-methyl-2-(3-pyridyl)-2-nonanol,
No. 62: 1-(4-methoxyphenylthio)-3-methyl-2-(3-pyridyl)-2-nonanol,
No. 63: 1-(beta-naphthylthio)-3-methyl-2-(3-pyridyl)-2-nonanol.

The formulae and physicochemical properties of these compounds are shown in Table I, placed at the end of the description. The structure of these compounds was confirmed by NMR.

In the case of Examples Nos. 2 to 4, 6, 30 to 35, 44 to 46, 49, 54 and 55, the yields as shown in Table I relate to the products obtained by recrystallisation in hexane according to the method of Example 1. In the case of compounds nos. 5, 7 to 29 and 36 to 43, 47, 48, 50 to 53 and 56 to 63, these yields relate to the products obtained by chromatography on a silica column with a hexane/ethyl acetate mixture as eluent.

The data which appear in the column "delta" are the values of the chemical shifts, in ppm, of the protons borne by the carbon atom located in the alpha-position with respect to the Ar-S- group, measured using TMS (tetramethylsilane) as internal reference, with the exception of Examples Nos. 3 to 8, 11, 45 and 58 to 60, for which HMDS (hexamethyldisiloxane) was used as internal reference.

EXAMPLE 64

Test in vivo on *Erysiphe graminis* on barley (barley mildew)

By fine grinding, there is prepared an aqueous emulsion of the active substance to be tested, having the following composition:

| | |
|---|---|
| active substance to be tested | 40 mg |
| Tween 80 (surfactant consisting of an oleate of a polycondensate of ethylene oxide with a sorbitan derivative) | 0.4 ml |
| water | 40 ml. |

This aqueous emulsion is then diluted with water to obtain the desired concentration.

Barley, sown in pots in a peat/pozzolana mixture is treated at the stage where it is 10 cm in height by spraying it with an aqueous emulsion at the concentration stated below. The trial is repeated twice. After 24 hours, the barley plants are dusted with *Erysiphe graminis* spores, the dusting being accomplished with the aid of diseased plants.

Readings are taken 10 days after contamination.

Under these conditions, good protection is observed with the compounds nos. 1, 11, 15, 16 and 45 at a dose of 330 ppm (parts per million). Good protection is obtained with compound no. 11 at a dose of 110 ppm.

EXAMPLE 65

Test in vivo on "Puccinia recondita" responsible for wheat rust

Wheat, sown in pots in a peat/pozzolana mixture, is treated at the stage where it is 10 cm in height by spraying it with aqueous emulsions of the same composition as that described in Example 64, and at various concentrations of the compound to be tested. The trial is repeated twice with each concentration.

After 24 hours, an aqueous suspension of spores (50,000 sp/cc) is sprayed onto the wheat; this suspension has been obtained from contaminated plants. The wheat is then placed for 48 hours in an incubation cell at approximately 18° C. and 100% relative humidity.

After these 2 days, the relative humidity is lowered to 60%. The condition of the plants is verified on the 15th day after contamination by comparison with the untreated control.

Under these conditions fairly good protection is observed with the compounds nos. 10, 11, 15, 36 and 63 used at a dose of 330 ppm, and good protection with the compounds Nos. 37, 58, 59, 60 and 61 used at the same dose.

EXAMPLE 66

Test on *Botrytis cinerea* on tomato

Greenhouse-cultivated tomatoes (Marmande variety) from 60 to 75 days old are treated by spraying them with aqueous emulsions of the same composition as that described in Example 65 and at various concentrations of the compound to be tested. The trial is repeated twice with each concentration.

After 24 hours, the leaves are cut and placed into 2 Petri dishes (diameter 11 cm) the base of which has been previously provided with a disc of damp filter paper (5 leaflets per dish).

The inoculum is then applied with the aid of a syringe by depositing drops (3 drops per leaflet) of a spore suspension. This suspension of spores of *Botrytis cinerea* has been obtained from a 15-day culture which has then been suspended in a nutrient solution (80,000 units/cc).

Vertification is carried out 4 days after contamination by comparison with an untreated control.

Under these conditions, complete protection is observed with the compounds nos. 36, 37, 38 and 44 used at a dose of 110 ppm.

Good protection is otained with the compounds nos. 12, 13, 16, 31, 40, 46, 50, 57, 58, 59 and 60 at a dose of 330 ppm.

EXAMPLE 67

Tests in vitro on seed fungi and soil fungi

The action of the compounds according to the invention is studied on the following fungi responsible for secondary diseases of cereals:

*Cercosporella herpotrichoides*: (CERC)
*Helminthosporium gramineum*: (HELM G)
*Pyrenophorae avenae*: (PYRE)
*Septoria nodorum*: (SEPT N)
*Helminthosporium teres*: (HELM T)
*Fusarium roseum*: (FUS ROS)
*Fusarium nivale*: (FUS NIV)
*Fusarium culmorum*: (FUS CULM)
*Rhizoctonia cerealis*: (RHIZ C)

The designations given in parenthesis will be used to denote these fungi in Table (II), placed at the end of the description.

For each trial, the procedure is as follows: nutrient medium (potato+dextrose+agar; 10 ml) is placed in test tubes, and each tube is then stoppered and sterilised at 120° C. for 20 min. The tubes are then placed in a water bath maintained at 60° C. Using a pipette, a specified amount of a 1% strength acetone solution of the compound to be tested is then injected into each tube, so as to obtain a specified concentration of this compound in the medium. After homogenisation, the supercooled medium present in each tube is poured aseptically into a Petri dish 5 cm in diameter.

After 24 hours, each dish is seeded by depositing a fragment of mycelium (approximately 8 mm in diameter) originating from a culture of the fungus in question.

As a control, a dish similar to the above is taken, but in which the nutrient medium does not contain active substance. The dishes are kept for 2 to 10 days (according to the fungus tested) at 22° C., and the growth of the fungus in the dishes containing the active substance to be tested is compared with that of the same fungus in the dish used as control.

For each compound tested, the dose is thus determined which caused almost complete inhibition (90-100%) of the growth of the fungus.

The compounds which cause almost complete inhibition of the growth of the fungi at 10 ppm are recorded in Table II, placed at the end of the description, in which the abbreviations have the significance given above.

The experiments described in Examples 64 to 67 clearly illustrate the good fungicidal properties of the compounds according to the invention.

These compounds can thus be used for both preventive and curative control of fungi, especially of the basidiomycetes, ascomycetes, adelomycetes or fungi imperfecti types, in particular rusts, mildews, fusarioses, helminthosporioses, septorioses and rhizoctones of vegetables and plants in general and, in particular, of cereals such as wheat, barley, rye, oats and their hybrids, and also rice and maize.

The products of the invention are particularly valuable by virtue of their broad spectrum in regard to diseases of cereals (mildew, rust, eyespot, helminthosporioses, septorioses and especially the fusarioses which are difficult to combat).

They are also very valuable, in addition to having a broad spectrum, by reason of their high activity towards Botrytis and, for this reason, they can be applied to crops as varied as vine, market-gardening crops and arboriculture.

They are advantageously applied at doses from 0.05 to 5 kg/ha, preferably from 0.1 to 2 kg/ha.

To use them in practice, the compounds according to the invention are rarely used alone. They most frequently form part of compositions. These compositions, which can be used for the protection of plants against fungal diseases, contain as an active substance a compound according to the invention, as described above, in combination with solid or liquid carriers which are acceptable in agriculture, and optionally with surfactants which are also acceptable in agriculture. The usual inert carriers and usual surfactants can, in particular, be used.

These compositions can also contain any other type of ingredient, e.g. protective colloids, adhesives, thickeners, thixotropic agents, penetrants, stabilisers, sequestering agents and the like, as well as other known active substances having pesticidal properties (especially insecticidal or fungicidal properties) or properties which encourage plant growth (especially fertilisers) or properties of regulating plant growth. More generally, the compounds according to the invention can be combined with all the solid or liquid additives which correspond to the customary techniques of formulation.

The doses for use can vary within broad limits according, in particular, to the virulence of the fungi and the climatic-conditions.

Compositions containing 0.5 to 5,000 ppm of active substance are generally very suitable, these values apply to the compositions ready for application. The range from 0.5 to 5,000 ppm is equivalent to a range from $5 \times 10^{-5}$ to 0.5% (percentages by weight).

As regards compositions intended for storage and transportation, these more advantageously contain from 0.5 to 95% (by weight) of active substance.

Thus, the compositions for agricultural use according to the invention can hence contain the active substances according to the invention within very broad limits, ranging from $5 \times 10^{-5}$% to 95% (by weight).

According to what has already been stated, the compounds according to the invention are generally present in combination with carriers and optionally with surfactants.

In the present account, the term "carrier" denotes an organic or inorganic, natural or synthetic material which is in combination with the active substance to facilitate the application of the latter to the plant, seeds or soil. This carrier is hence generally inert, and it must be acceptable in agriculture, especially on the plant treated. The carrier can be solid (clays, natural or synthetic silicates, silica, resins, waxes, solid fertilisers, and the like) or liquid (water, alcohols, ketones, petroleum fractions, aromatic or paraffinic hydrocarbons, chlorinated hydrocarbons, liquefied gases, and the like).

The surfactant can be an emulsifier, dispersant or wetting agent of ionic or nonionic type. There may be mentioned, e.g., salts of polyacrylic acids, salts of lignosulphonic acids, salts of phenolsulphonic or naphthalenesulphonic acids, polycondensates of ethylene oxide with fatty alcohols or fatty acids or fatty amines, substituted phenols (especially alkylphenols or arylphenols), salts of sulphosuccinic acid esters, taurine derivatives (especially alkyltaurates), and phosphoric acid esters of polycondensates of ethylene oxide with alcohols or phenols. The presence of at least one surfactant is generally essential when the active substance and/or the inert carrier are not water-soluble and the vector agent for the application is water.

For their application, the compounds of formula (I) are generally in the form of compositions; these compositions according to the invention are themselves in fairly diverse solid or liquid forms.

As solid forms of compositions, there may be mentioned powders for dusting or scattering (with a content of the compound of formula (I) ranging up to 100%) and pellets, especially those obtained by extrusion, by compacting, by impregnation of a granulated carrier, or by granulation starting from a powder [the content of the compound of formula (I) in these pellets being between 1 and 80% in the latter cases].

As liquid forms of compositions, or forms designed to constitute liquid compositions when applied, there may be mentioned solutions, especially water-soluble concentrates, emulsifiable concentrates, emulsions, flowables, aerosols, wettable powders (or powder for spraying) and pastes.

The emulsifiable or soluble concentrates most frequently contain 10 to 80% of active substance, whereas the emulsions or solutions ready for application contain 0.01 to 20% of active substance. In addition to the solvent, the emulsifiable concentrates can contain, when, necessary, a suitable co-solvent and from 2 to 20% of suitable additives such as stabilisers, surfactants, penetrants, corrosion inhibitors, colourings and adhesives. By way of example, the composition of a few emulsifiable concentrates is as follows:

| | |
|---|---|
| active substances | 400 g/l |
| alkali metal dodecylbenzenesulphonate | 24 g/l |
| 10:1 ethylene oxide/nonylphenol condensate | 16 g/l |
| cyclohexanone | 200 g/l |
| aromatic solvent q.s. | 1 liter. |

According to another formula for an emulsifiable concentrate, there are used:

| | |
|---|---|
| active substance | 250 g |
| epoxide-treated vegetable oil | 25 g |
| mixture of alkylaryl sulphonate, polyglycol ether and fatty alcohols | 100 g |
| dimethylformamide | 50 g |
| xylene | 575 g |

From these concentrates, by dilution with water, it is possible to obtain emulsions of any desired concentration, which are especially suitable for application to leaves.

Flowables, which can also be applied by spraying, are prepared so as to obtain a stable fluid product which does not settle, and they usually contain from 10 to 75% of active substance, from 0.5 to 15% of surfactants, from 0.1 to 10% of thixotropic agents, from 0 to 10% of suitable additives such as antifoams, corrosion inhibitors, stabilisers, penetrants and adhesives and, as a carrier, water or an organic liquid in which the active substance is of low solubility or insoluble: some solid organic substances or inorganic salts can be dissolved in the carrier to assist in preventing sedimentation, or as anti-freeze for the water.

The wettable powders (or powder for spraying) are usually prepared so as to contain 20 to 95% of active substance, and they usually contain, in addition to the active substance and the solid carrier, from 0 to 5% of a wetting agent, from 3 to 10% of a dispersant and, when necessary, from 0 to 10% of one or more stabilisers and/or other additives such as penetrants, adhesives, or anti-caking agents, colourings, and the like.

By way of example, various compositions of wettable powders are as follows:

| | |
|---|---|
| active substance | 50% |
| calcium lignosulphonate (deflocculant) | 5% |
| isopropyl naphthalenesulphonate (anionic wetting agent) | 1% |
| anti-caking silica | 5% |
| kaolin (filler) | 39% |

Another composition of powder for spraying, at 70% strength, uses the following constituents:

| | |
|---|---|
| active substance | 700 g |
| sodium dibutylnaphthalenesulphonate | 50 g |
| condensation product of naphthalenesulphonic acid, phenolsulphonic acid and formaldehyde in proportions 3:2:1 | 30 g |
| kaolin | 100 g |
| whitening | 120 g |

Another composition of powder for spraying, at 40% strength, uses the following constituents:

| | |
|---|---|
| active substance | 400 g |
| sodium lignosulphonate | 50 g |
| sodium dibutylnaphthalenesulphonate | 10 g |
| silica | 540 g |

Another composition of powder for spraying, at 25% strength, uses the following constituents:

| | |
|---|---|
| active substance | 250 g |
| calcium lignosulphonate | 45 g |
| mixture of whitening and hydroxyethylcellulose in equal parts by weight | 19 g |
| sodium dibutylnaphthalenesulphonate | 15 g |
| silica | 195 g |
| whitening | 195 g |
| kaolin | 281 g |

Another composition of powder for spraying, at 25% strength, uses the following constituents:

| | |
|---|---|
| active substance | 250 g |
| isooctylphenoxy-polyoxyethylene-ethanol | 25 g |
| mixture of whitening and hydroxyethylcellulose in equal parts by weight | 17 g |
| sodium aluminosilicate | 543 g |
| kieselguhr | 165 g |

Another composition of powder for spraying, at 10% strength, uses the following constituents:

| | |
|---|---|
| active substance | 100 g |
| mixture of sodium salts of sulphates of saturated fatty acids | 30 g |
| condensation product of naphthalenesulphonic acid and formaldehyde | 50 g |
| kaolin | 820 g |

To obtain these powders for spraying or wettable powders, the active substances are intimately mixed in suitable mixers with the additional substances, and the mixtures are ground in suitable mills or other grinders. Powders for spraying are thereby obtained, the wettability and suspendability of which are advantageous; they can be suspended in water at any desired concentration and this suspension can be very advantageously used, especially for application to plant leaves.

Instead of wettable powders, pastes can be produced. The conditions and methods of production and use of these pastes are similar to those for wettable powders or powders for spraying.

As already stated, the dispersions and aqueous emulsions, e.g. the compositions obtained by diluting with water a wettable powder or an emulsifiable concentrate according to the invention, are included within the general scope of the present invention. The emulsions can be of the water-in-oil or oil-in-water type, and they can have a thick consistency like that of "mayonnaise".

Pellets intended for placing on the soil are usually prepared so as to be between 0.1 and 2 mm in size, and they can be manufactured by agglomeration or impregnation. In general, the pellets contain 0.5 to 25% of active substance and 0 to 10% of additives such as stabilisers, slow release modification agents, binders and solvents.

According to an example of a pellet composition, the following constituents are used:

| | |
|---|---|
| active substance | 50 g |
| epichlorohydrin | 2.5 g |
| cetyl polyglycol ether | 2.5 g |
| polyethylene glycol | 35 g |
| kaolin (particle size: 0.3 to 0.8 mm) | 910 g |

In this particular case, the active substance is mixed with the epichlorohydrin and dissolved in 60 g of acetone; the polyethylene glycol and cetyl polyglycol ether are then added. The kaolin is wetted with the solution obtained and the acetone is then evaporated under vacuum. Such a micropellet is advantageously used to control soil fungi.

The compounds of formula (I) can further be used in the form of powders for dusting; a composition comprising 50 g of active substance and 950 g of talc can also be used; a composition comprising 20 g of active substance, 10 g of finely divided silica and 970 g of talc can also be used; these constituents are mixed and ground, and the mixture is applied by dusting.

The invention also relates to a process for controlling fungal diseases of plants. This process consists in applying to these plants an effective amount of a composition containing as active substance a compound of formula (I). By "effective" amount, there is understood an amount sufficient to combat the fungal disease without damaging the treated plants. The doses for use can vary within wide limits according to the fungus to be combated, the type of crop, the climatic conditions and the compound used. As stated above, these doses are advantageously between 0.05 and 5 kg/ha.

TABLE I $$Ar-S-CH_2-\underset{\underset{R}{|}}{\overset{\overset{OH}{|}}{C}}-\diagup\!\!\diagdown\!\!\diagup N$$

| Example | Ar | R | Yield (%) | Melting point | delta ppm |
|---|---|---|---|---|---|
| 1 | p-CH$_3$—C$_6$H$_4$— | —C(CH$_3$)$_3$ | 57% | 67° C. | |
| 2 | p-Br—C$_6$H$_4$— | H | 70% | 89° C. | 3.20 |
| 3 | p-CF$_3$—C$_6$H$_4$— | H | 31% | 73° C. | 3.24 |
| 4 | p-Cl—C$_6$H$_4$— | —CH$_3$ | 59% | 75° C. | 3.39–3.25 |
| 5 | p-CF$_3$—C$_6$H$_4$— | —CH$_3$ | 37% | oil | 3.45–3.33 |
| 6 | p-Br—C$_6$H$_4$— | —CH$_3$ | 93% | 57° C. | 3.34–3.24 |
| 7 | p-CH$_3$—C$_6$H$_4$— | —CH$_3$ | 58% | oil | 3.34–3.23 |
| 8 | o,p-Cl$_2$—C$_6$H$_3$— | —CH$_3$ | 46% | oil | 3.29–3.23 |
| 9 | β-naphthyl | —CH$_3$ | 100% | oil | 3.41–3.25 |
| 10 | β-naphthyl | —C$_6$H$_5$ | 57% | oil | 4.00–3.85 |
| 11 | p-Cl—C$_6$H$_4$— | —C$_6$H$_5$ | 35% | oil | 3.78–3.68 |
| 12 | p-CF$_3$—C$_6$H$_4$— | —C$_6$H$_5$ | 27% | oil | 4.00–3.77 |
| 13 | p-Br—C$_6$H$_4$— | —C$_6$H$_5$ | 62% | oil | 3.90–3.67 |
| 14 | β-naphthyl; | p-Cl—C$_6$H$_4$— | 33% | oil | 4.00–3.77 |
| 15 | p-Cl—C$_6$H$_4$— | p-Cl—C$_6$H$_4$— | 37% | oil | 3.90–3.67 |
| 16 | p-Br—C$_6$H$_4$— | p-Cl—C$_6$H$_4$— | 67% | oil | 3.87–3.67 |
| 17 | p-CH$_3$—C$_6$H$_4$— | p-Cl—C$_6$H$_4$— | 14% | oil | 3.82–3.67 |
| 18 | p-Cl—C$_6$H$_4$— | p-Br—C$_6$H$_4$— | 59% | oil | 3.82–3.65 |
| 19 | p-CH$_3$—C$_6$H$_4$— | p-Br—C$_6$H$_4$— | 32% | oil | 3.85–3.65 |
| 20 | p-Br—C$_6$H$_4$— | p-Br—C$_6$H$_4$— | 31% | oil | 3.85–3.62 |
| 21 | C$_6$H$_5$— | p-Br—C$_6$H$_4$— | 53% | oil | 3.90–3.70 |
| 22 | m-Cl,p-CH$_3$—C$_6$H$_3$— | p-Br—C$_6$H$_4$— | 44% | oil | 3.75–3.62 |
| 23 | p-Br—C$_6$H$_4$— | —CH(CH$_3$)$_2$ | 47% | oil | 3.70–3.35 |
| 24 | p-CF$_3$—C$_6$H$_4$— | —CH(CH$_3$)$_2$ | 49% | oil | 3.72–3.38 |
| 25 | p-Cl—C$_6$H$_4$— | —CH(CH$_3$)$_2$ | 62% | oil | 3.70–3.37 |
| 26 | p-Br—C$_6$H$_4$— | —CH$_2$—CH(CH$_3$)$_2$ | 56% | oil | 4.00–3.38 |
| 27 | p-Cl—C$_6$H$_4$— | —CH$_2$—CH(CH$_3$)$_2$ | 47% | oil | 4.02–3.40 |
| 28 | p-CF$_3$—C$_6$H$_4$— | —CH$_2$—CH(CH$_3$)$_2$ | 52% | oil | 3.98–3.35 |
| 29 | p-Cl—C$_6$H$_4$— | —H | 66% | oil | 3.20 |
| 30 | p-Cl—C$_6$H$_4$— | —C(CH$_3$)$_3$ | 67% | oil | 4.04–3.36 |
| 31 | p-Br—C$_6$H$_4$— | —C(CH$_3$)$_3$ | 71% | oil | 4.00–3.37 |
| 32 | 3,5-Cl$_2$—C$_6$H$_3$— | —C(CH$_3$)$_3$ | 24% | 116° C. | 3.69–3.10 |
| 33 | p-F—C$_6$H$_4$— | —C(CH$_3$)$_3$ | 48% | 68° C. | 4.03–3.30 |
| 34 | o-CH$_3$,p-Cl—C$_6$H$_3$ | —C(CH$_3$)$_3$ | 43% | 136° C. | 3.96–3.30 |
| 35 | β-naphthyl | —C(CH$_3$)$_3$ | 52% | 74° C. | 4.12–3.48 |
| 36 | p-Cl—C$_6$H$_4$— | —CH(CH$_3$)—C$_2$H$_5$ | 66% | oil | 3.85–3.40 |
| 37 | p-Br—C$_6$H$_4$— | —CH(CH$_3$)C$_2$H$_5$ | 66% | oil | 3.95–3.42 |
| 38 | p-CH$_3$—C$_6$H$_4$— | —CH(CH$_3$)—C$_2$H$_5$ | 70% | oil | 3.71–3.77 |
| 39 | o-CH$_3$,p-Cl—C$_6$H$_3$— | —CH(CH$_3$)—C$_2$H$_5$ | 60% | oil | 3.80–3.38 |
| 40 | p-CH$_3$O—C$_6$H$_4$ | —CH(CH$_3$)—C$_2$H$_5$ | 74,5% | oil | 3.68–3.32<br>3.68–3.31 |
| 41 | p-F—C$_6$H$_4$ | —CH(CH$_3$)—C$_2$H$_5$ | 91,5% | oil | 3.67–3.38<br>3.65–3.38 |
| 42 | p-nC$_{12}$H$_{25}$—C$_6$H$_4$ | —CH(CH$_3$)—C$_2$H$_5$ | 96,5% | oil | 3.48–3.81<br>3.46–3.81 |
| 43 | p-nC$_9$H$_{19}$—C$_6$H$_7$ | —CH(CH$_3$)—C$_2$H$_5$ | 94% | oil | 3.41–3.72<br>3.39–3.72 |
| 44 | p-CF$_3$—C$_6$H$_4$ | —CH(CH$_3$)—C$_2$H$_5$ | 11% | 87° C. | 3.51–3.75<br>3.49–3.75 |
| 45 | 2,4,5-Cl$_3$—C$_6$H$_2$ | —CH(CH$_3$)—C$_2$H$_5$ | 15% | 116° C. | 3.65–3.33<br>3.63–3.31 |
| 46 | β-naphthyl | —CH(CH$_3$)—C$_2$H$_5$ | 70% | 105° C. | 3.51–3.77<br>3.49–3.77 |
| 47 | p-nC$_{12}$H$_{25}$—C$_6$H$_4$ | —C(CH$_3$)$_3$ | 53,5% | oil | 3.35–4.05 |
| 48 | p-nC$_9$H$_{19}$—C$_6$H$_4$ | —C(CH$_3$)$_3$ | 46% | oil | 3.34–4.04 |
| 49 | 2,4Cl$_2$—C$_6$H$_3$ | —C(CH$_3$)$_3$ | 17% | 131° C. | 3.29–4.05 |
| 50 | β-naphthyl | —C(CH$_3$)$_2$—C$_2$H$_5$ | 30% | oil | 3.47–4.13 |
| 51 | p-F—C$_6$H$_4$ | —C(CH$_3$)$_2$—C$_2$H$_5$ | 32% | oil | 3.32–4.02 |
| 52 | p-nC$_{12}$H$_{25}$—C$_6$H$_4$ | —C(CH$_3$)$_2$—C$_2$H$_5$ | 30% | oil | 3.36–4.08 |
| 53 | p-C$_9$H$_{19}$—C$_6$H$_4$ | —C(CH$_3$)$_2$—C$_2$H$_5$ | 25% | oil | 3.36–4.06 |
| 54 | p-Br—C$_6$H$_4$ | —C(CH$_3$)$_2$—C$_2$H$_5$ | 20% | 119° C. | 3.36–4.07 |

TABLE I-continued $$Ar-S-CH_2-\underset{\underset{R}{|}}{\overset{\overset{OH}{|}}{C}}-\underset{}{\underset{}{\text{pyridyl}}}$$

| Example | Ar | R | Yield (%) | Melting point | delta ppm |
|---|---|---|---|---|---|
| 55 | p-Cl—$C_6H_4$ | —$C(CH_3)_2$—$C_2H_5$ | 17% | 108° C. | 3.34–4.05 |
| 56 | p-$CH_3$—$C_6H_4$ | —$C(CH_3)_2$—$C_2H_5$ | 15% | oil | 3.32–4.02 |
| 57 | p-$CH_3O$—$C_6H_4$ | —$C(CH_3)_2$—$C_2H_5$ | 30,5% | oil | 3.25–4.01 |
| 58 | p-Cl—$C_6H_4$ | —$CH(CH_3)nC_3H_7$ | 52,5% | oil | 3.63–3.36 3.60–3.34 |
| 59 | p-Br—$C_6H_4$ | —$CH(CH_3)nC_3H_7$ | 47,5% | oil | 3.59–3.37 3.58–3.36 |
| 60 | p-$CF_3$—$C_6H_4$ | —$CH(CH_3)nC_3H_7$ | 24,5% | oil | 3.68–3.46 3.65–3.45 |
| 61 | p-Br—$C_6H_4$ | —$CH(CH_3)nC_6H_{13}$ | 29,5% | oil | 3.82–3.42 3.80–3.41 |
| 62 | p-$CH_3O$—$C_6H_4$ | —$CH(CH_3)nC_6H_{13}$ | 27% | oil | 3.72–3.32 3.71–3.31 |
| 63 | β-naphthyl | —$CH(CH_3)nC_6H_{13}$ | 10% | oil | 3.82–3.53 3.80–3.52 |

TABLE II

| FUNGI | COMPOUNDS INHIBITING THE GROWTH OF FUNGI AT A DOSE OF 10 PPM |
|---|---|
| CERC | 2-23-26-27-31-36-37-38-39-40-41-44-49-50-51-54-55-56-57-58-59-60 |
| HELM-G | 23-26-27-30-31-37-38-39-44-46-49-54-55-56-57-58-59-60 |
| PYRE | 23-26-27-30-31-36-37-38-39-40-44-46-49-51-54-55-56-57-58-59-60 |
| HELM-T | 10-13-23-26-27-30-31-36-37-38-39-40-41-44-46-49-50-51-54-55-56-57-58-59-60 |
| SEPT-N | 1-17-23-26-27-30-31-36-37-38-39-40-41-44-46-49-51-54-55-56-57-58-59-60 |
| FUS-ROS | 1-36-37-38-46 |
| FUS-NIV | 12 |
| FUS-CULM | 1-12-23-26-36-38-40-41-44-49-50-51-54-55-56-57-58-59-60 |
| RHIZ-C | 1-30-56-60 |

We claim:

1. An (arylthio)pyridylalkanol derivative of the general formula (I):

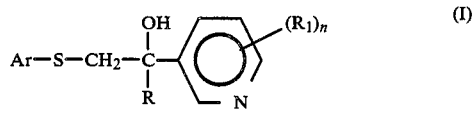

in which:

Ar denotes an aryl radical containing 6 to 10 carbon atoms, said aryl radical being optionally substituted with one or more identical or different atoms or radicals chosen from halogen atoms; alkyl radicals containing 1 to 12 carbon atoms, said alkyl radicals being optionally mono- or polyhalogenated; alkenyl and alkynyl radicals containing 3 to 12 carbon atoms; alkoxy and alkylthio radicals containing 1 to 6 carbon atoms, said alkoxy and alkylthio radicals being optionally mono- or polyhalogenated; cyano radicals; nitro radicals; phenyl radicals, said phenyl radicals being optionally mono- or polyhalogenated; benzyl radicals; phenoxy radicals and amino radicals, said amino radicals being optionally substituted with 1 to 2 alkyl radicals having from 1 to 6 carbon atoms and alkanoyl radicals having from 2 to 6 carbon atoms;

R denotes a hydrogen atom or an alkyl radical containing 1 to 10 carbon atoms; a phenyl radical or a benzyl radical, said phenyl radical and said benzyl radical being optionally substituted with one or more halogen atoms or one or more alkyl radicals each containing 1 to 6 carbon atoms;

$R_1$ denotes an alkyl radical containing 1 to 6 carbon atoms;

and n equals 0, 1, 2, 3 or 4, on the understanding that when n is greater than 1, the substituents $R_1$ can be either identical or different, and salified forms of said derivative.

2. A compound according to claim 1, in which R denotes a branched alkyl radical containing 3 to 5 carbon atoms.

3. A composition which can be used for protecting plants against fungal diseases, which contains as active substance an effective amount of a compound according to one of claims 1 or 2.

4. A composition according to claim 3, which contains, in addition to an effective amount of the active substance, one or more carriers acceptable in agriculture and/or one or more surfactants acceptable in agriculture.

5. A composition according to claim 4, which contains from 0.5 to 95% by weight of active substance.

6. A process for controlling fungal diseases of plants, which consists in applying to the plants an effective amount of a compound according to one of claims 1 or 2.

* * * * *

UNITED STATES PATENT AND TRADEMARK OFFICE
CERTIFICATE OF CORRECTION

PATENT NO. : 4,677,128
DATED : June 30, 1987
INVENTOR(S) : Pierre Place, et al.

It is certified that error appears in the above-identified patent and that said Letters Patent is hereby corrected as shown below:

Column 6, line 35: "-2-(pyridyl)-" should read as -- -2-(3-pyridyl)- --

Signed and Sealed this

Eighth Day of December, 1987

Attest:

DONALD J. QUIGG

Attesting Officer          Commissioner of Patents and Trademarks